(12) United States Patent
Malcolm et al.

(10) Patent No.: US 6,951,654 B2
(45) Date of Patent: Oct. 4, 2005

(54) INTRAVAGINAL DRUG DELIVERY DEVICES FOR THE ADMINISTRATION OF AN ANTIMICROBIAL AGENT

(75) Inventors: Karl Malcolm, Belfast (IE); David Woolfson, Belfast (IE); Grant Elliott, Islandmagee (IE); Martin Shephard, Belfast (IE)

(73) Assignee: Galen (Chemicals) Limited, Dublin (IE)

(*) Notice: Subject to any disclaimer, the term of this patent is extended or adjusted under 35 U.S.C. 154(b) by 471 days.

(21) Appl. No.: 10/107,997

(22) Filed: Mar. 27, 2002

(65) Prior Publication Data

US 2003/0059456 A1 Mar. 27, 2003

(30) Foreign Application Priority Data

Mar. 27, 2001 (IE) .......................................... S2001/0307

(51) Int. Cl.[7] .............................. A61F 6/06; A61F 6/14
(52) U.S. Cl. ........................................ 424/430; 424/432
(58) Field of Search ................................. 424/430, 432

(56) References Cited

U.S. PATENT DOCUMENTS

| | | | |
|---|---|---|---|
| 4,012,497 A | 3/1977 | Schopflin | 424/22 |
| 4,155,991 A * | 5/1979 | Schopflin et al. | 424/432 |
| 4,199,574 A | 4/1980 | Schaeffer | 424/200 |
| 4,358,449 A | 11/1982 | Heeres et al. | 424/248.58 |
| 4,404,216 A | 9/1983 | Richardson | 424/269 |
| 4,416,682 A | 11/1983 | Worthington | 71/76 |
| 4,661,493 A | 4/1987 | Gibbs | 514/252 |
| 4,816,470 A | 3/1989 | Dowle et al. | 514/415 |
| 4,983,393 A | 1/1991 | Cohen et al. | 424/430 |
| 5,037,845 A | 8/1991 | Oxford | 514/415 |
| 5,069,906 A | 12/1991 | Cohen et al. | 424/430 |
| 5,295,984 A | 3/1994 | Contente et al. | 604/317 |
| 5,382,600 A | 1/1995 | Jönsson et al. | 514/603 |
| 5,482,965 A | 1/1996 | Rajadhyaksha | 514/452 |
| 5,532,278 A | 7/1996 | Aberg et al. | 514/617 |
| 5,559,269 A | 9/1996 | Johansson et al. | 564/443 |
| 5,607,691 A | 3/1997 | Hale et al. | 424/449 |
| 5,677,346 A | 10/1997 | Aberg et al. | 51/617 |
| 5,736,577 A | 4/1998 | Aberg et al. | 514/617 |
| 5,747,065 A | 5/1998 | Lee et al. | 424/448 |
| 5,788,980 A | 8/1998 | Nabahi | 424/430 |
| 5,840,744 A | 11/1998 | Borgman | 514/398 |
| 5,900,250 A | 5/1999 | Lee et al. | 424/448 |
| 6,004,582 A | 12/1999 | Faour et al. | 424/473 |
| 6,039,968 A | 3/2000 | Nabahi | 424/433 |
| 6,103,256 A | 8/2000 | Nabahi | 424/430 |
| 6,194,591 B1 | 2/2001 | Grey et al. | 549/533 |
| 6,255,502 B1 | 7/2001 | Penkler et al. | 552/549 |
| 6,410,546 B1 | 6/2002 | Furman et al. | 514/274 |

FOREIGN PATENT DOCUMENTS

WO    WO92/18101    * 10/1992

OTHER PUBLICATIONS

British National Formulary, pp. 280–281, (2000).
Merck Index, 11th Edition, pp. 6079, (1989).
Chien, Y. Et al., "Fundamentals of Rate–Controlled Drug Delivery", 2nd Edition, Marcel Dekker, New York, pp. 43–137, (1992).
Zatuchni et al., Vaginal Contraception: Proceedings of an International Workshop on New Developments In Vaginal Contraception, pp. 201–208, (1979).
Acta dermato–venereologica: An international Journal for Skin Research, Clinical Dermatology and Sexually Transmitted Diseases, vol. 79, No. 5, pp. 414–415, (1999).
A. Tsuji et al., "Development of Antibiotic Releasing Intravaginal Drug Delivery System," Proceedings of the International Congress of Chemotherapy, vol. 9, No. 124, 84–87 (1983).

* cited by examiner

*Primary Examiner*—Carlos A. Azpuru
(74) *Attorney, Agent, or Firm*—Fitzpatrick, Cella, Harper & Scinto

(57) ABSTRACT

An intravaginal antimicrobial drug delivery device is disclosed having an antimicrobial agent dispersed throughout a biocompatible elastomeric system. Also disclosed is a method of making the antimicrobial drug delivery device.

42 Claims, 4 Drawing Sheets

INTRAVAGINAL DRUG DELIVERY DEVICES FOR THE ADMINISTRATION OF AN ANTIMICROBIAL AGENT

BACKGROUND OF THE INVENTION

1. Field of the Invention

This invention relates to intravaginal drug delivery devices for the administration of an antimicrobial agent or a mixture thereof. Preferably, it relates to intravaginal drug delivery devices for the treatment or prevention of a disease condition exacerbated by a bacterial, fungal, viral, and/or protozoal infection in a human or other animal female. In particular, it relates to intravaginal drug delivery devices, such that, for example, the symptoms associated with a vaginal disease condition of, for example, bacterial, fungal, viral and/or protozoal origin may be alleviated. Alternatively, the invention relates to intravaginal drug delivery devices for the local treatment of a disease condition, preferably a vaginal disease condition. Most preferably, the invention relates to the intravaginal delivery of quinolones, macrolides, clindamycin, tetracyclines, antibacterial and antifungal imidazoles and antiviral agents such as acyclovir, for the treatment of vaginitis of bacterial, fungal, viral and/or protozoal origin in a human female.

2. Related Background Art

Vaginitis (microbial infection of the human vagina) is the most common gynaecological problem encountered in the human female within the primary healthcare setting. Vaginitis is predominantly due to infections of bacterial, fungal (including yeast), viral and/or protozoal origins.

Bacterial vaginosis (non-specific vaginitis) is the most common type of bacterial vaginitis in women (Petersen, C. S et al, Acta Dermato-Venereologica Vol. 79, pp. 414–415, 1999), representing about 40% of all vaginitis. Bacterial vaginosis is a polymicrobial, primarily anaerobic, infection and is associated with a reduction in *Lactobacillus* species, together with a massive overgrowth in anaerobic microorganisms, notably *Gardnerella vaginalis* and *Chlamydia trachomatis* and certain *Prevotella* and *Mobiluncus* species. Opportunistic species such as *Staphylococcus epidermidis* and *Enterococcus faecalis* may also appear.

*Trichomonas vaginalis* is a single-celled protozoal parasite of the human vagina. It is the organism responsible for trichomoniasis, a further aspect of the collective condition referred to as vaginitis. Approximately one in five human females will develop trichomoniasis at some point during their reproductive years.

Metronidazole has long been taken by the oral route for these conditions but orally administered metronidazole is associated with a range of unpleasant side effects, i.e. nausea and vomiting, gastrointestinal disturbances, headache, peripheral neuropathy, in addition to a disulfiram-like reaction in the presence of alcohol (British National Formulary 2000). Local intravaginal administration of an antimicrobial agent such as metronidazole might be expected to avoid most of these unwanted side effects.

Intravaginal drug delivery systems generally fall into two main groups, those adapted from semi-solid topical systems (usually applied using a vaginal applicator device) and those designed specifically for intravaginal use. The former, which are semi-solids, include semi-solid ointments, creams and gels. U.S. Pat. No. 5,840,744 describes an intravaginal preparation of the former group in the form of a non-flowing gel containing 375 mg or less of metronidazole dispersed in a polyacrylic acid polymer. An intravaginal semi-solid preparation of metronidazole is also commercially available as METROGEL-VAGINAL (Trade Mark), containing 0.75 g % by weight of the drug. The recommended dose for the treatment of bacterial vaginosis is 37.5 mg once or twice daily, applied for a five day period using an intravaginal applicator containing, for each dose, approximately 5 g of gel. This yields a total dose of 187.5 mg or 375 mg metronidazole over the 5 day treatment period.

Other examples of semi-solid topical systems for vaginal application include CANESTAN (Trade Mark) cream, containing 1% Clotrimazole with a suggested daily dose of about 500 mg; CLEOCIN/DALACIN (Trade Marks) cream, containing 2% Clindamycin (as phosphate) with a suggested daily dose of 100 mg; ECOSTATIN or PEVARYL (Trade Marks) creams containing 1% Econazole Nitrate; GYNO-DAKTARIN (Trade Mark) cream containing 2% Miconazole Nitrate; SULTRIN (Trade Mark) cream containing 3.4% Sulphathiazole, 2.8% Sulphacetamide and 3.7% Sulphabenzamide; NIZORAL (Trade Mark) cream containing 2% Ketoconazole with a suggested daily dose of about 100 mg; and TERAZOLE (Trade Mark) cream containing 0.8% Terconazole with a suggested daily dose of 40 mg.

Intravaginal administration of antimicrobial agents such as metronidazole, clindamycin, clotrimazole and econazole in the form of such a semi-solid topical preparation, although offering advantages over the oral route in respect of avoiding some unwanted side effects, nevertheless suffers from several disadvantages.

These are:

Patient compliance is problematic, since such intravaginal gel preparations currently require once or twice daily applications over a 5 day period using specially designed applicators. Additionally, it is not possible for the patient to immediately terminate the treatment at any time by removal of the semi-solid topical preparation, in the event of any adverse reaction being noted.

Messiness during application of such a semi-solid preparation. In addition, given the volume of material to be delivered intravaginally and their rheological characteristics, semi-solid preparations will leak from the vaginal space following administration so that the available concentration of active agent in solution within the vaginal space will be non-optimal and non-constant for a prolonged period of time.

Where resistant isolates arise, a higher drug loading is needed since the minimum inhibitory concentration of the drug which, for metronidazole, for example, is greater than the 128 $\mu$g per ml in solution of normal drug-sensitive isolates.

Many of the problems associated with intravaginal delivery of metronidazole and other antimicrobial agents for the treatment or prevention of a susceptible disease condition such as bacterial vaginosis or the like could be overcome by the use of an intravaginal drug delivery device, not selected from those adapted from semi-solid topical systems but, rather, selected from those designed specifically for intravaginal use. The latter, being systems designed for intravaginal use, include tablets, pessaries, rod-shapes, ring-shapes and films for adhesion to the mucosal epithelium. While these latter systems can be based on compressed powders, hydrogels, waxes or elastomers, the present invention concerns itself solely with those latter systems formed from elastomers.

Known pessary-type systems for vaginal application include BETADINE (Trade Mark) pessaries for twice-daily administration; GYNO-DAKTARIN 1 (Trade Mark) vaginal ovules for single dose administration; GYNO-DAKTARIN 1 (Trade Mark) pessaries for once-daily administration; and GYNO-PEVARYL 1 (Trade Mark) pessaries for single dose administration. These known pessary-type systems, however, also suffer from poor patient compliance since they either must be repeatedly administered over a prolonged period of time or, if a single dose, do not deliver sufficient antimicrobial agent. Such pessary-type systems are not elastomeric systems.

Intravaginal elastomer drug delivery devices, designed to deliver steroidal sex hormones, are well known in the art. Jackanicz (Jackanicz, T. M., Vaginal Contraception: New Developments. Harper and Row, Hagerstown, pp. 201–212, 1979) teaches that three basic designs of intravaginal elastomer drug delivery device are possible, though additional design variations do exist. The three basic types are the homogeneous design, the shell design and the core design:

a) The homogeneous or "matrix" design, in which the active agent is homogeneously distributed in an elastomeric system. This design provides for an exponential (first order) release decay, characterised by an initial high release of drug, followed by a lower release rate of drug. This design cannot sustain a controlled, substantially constant drug release rate, which will be recognised by those skilled in the art as "zero order release", over a prolonged period. Current teaching discourages the use of such "matrix" designs since a controlled substantially constant "zero order" drug release rate is now preferred.

b) The shell design, in which the active agent is contained in a narrow band between a non-medicated central elastomeric core and a narrow, outer non-medicated elastomeric sheath.

c) The core design, in which the active agent is homogeneously mixed with an elastomeric polymer to form a homogeneous core, the whole being surrounded by a rate controlling, non-medicated hydrophobic elastomeric sheath.

Intravaginal elastomer drug delivery devices of the shell or core design are currently preferred for the delivery of steroidal sex hormones, in that they facilitate substantially constant (or zero order) oestrogen and/or progestogen release over a prolonged period of time.

There is no teaching in the scientific or patent literature that an intravaginal elastomeric drug delivery device may deliver a non-steroidal antimicrobial agent for treating or preventing a susceptible disease condition such as vaginitis of susceptible bacterial, fugal, viral and/or protozoal origins. This is despite intravaginal elastomeric drug delivery devices being known to those skilled in the art and the clinical benefits of intravaginal application of antimicrobial agents such as metronidazole, clindamycin, clotrimazole or econazole, albeit from a semi-solid topical system or a non-elastomeric solid delivery system, being similarly known for many years.

Many of the problems associated with treatment or prevention of a susceptible disease condition such as bacterial vaginosis or the like could be overcome by incorporating an antimicrobial agent in a suitable intravaginal elastomer drug delivery device of matrix design. Such a device would be capable of releasing the agent under first order release decay in an initially high "loading" rate, which is desired for an antimicrobial agent, followed by a lower "maintenance" rate over several days such that, in use, the fluid in the vaginal space contains the antimicrobial agent at a concentration above its minimum inhibitory concentration.

SUMMARY OF THE INVENTION

Accordingly, the invention provides, in a first aspect, an intravaginal drug delivery device comprising an antimicrobial agent or a mixture thereof dispersed in an elastomer or a mixture thereof, the device being of matrix design.

This invention is directed to an intravaginal drug delivery device comprising a therapeutically effective amount of at least one antimicrobial agent dispersed throughout a biocompatible elastomeric system that forms the delivery device, i.e., the device is a matrix device. It is preferable for the elastomeric system to be hydrophobic. Preferably, the device of this invention takes the shape of a ring and most preferably the antimicrobial agent is a water soluble antimicrobial agent such as Metronidazole. Advantageously, the at least one antimicrobial agent is homogeneously dispersed in the elastomeric system.

Another embodiment of this invention is directed to a method of preparing the device of this invention. Significantly, the intravaginal antimicrobial drug delivery device of this invention provides a substantially first order release of the antimicrobial agent for about the first twenty four hours after insertion in a vaginal space followed by at least three days of substantially zero order release. Accordingly, the device of this invention provides a means of treating vaginitis in a convenient and high compliance manner with a preferred dosing strategy.

BRIEF DESCRIPTION OF THE DRAWINGS

FIG. 3 is a cumulative release profile illustrating the total amount of Metronidazole (mg) released in vitro over time for Examples 7 and 8 when compared with Examples 1 and 7a.

DETAILED DESCRIPTION OF THE INVENTION

Figure 1:
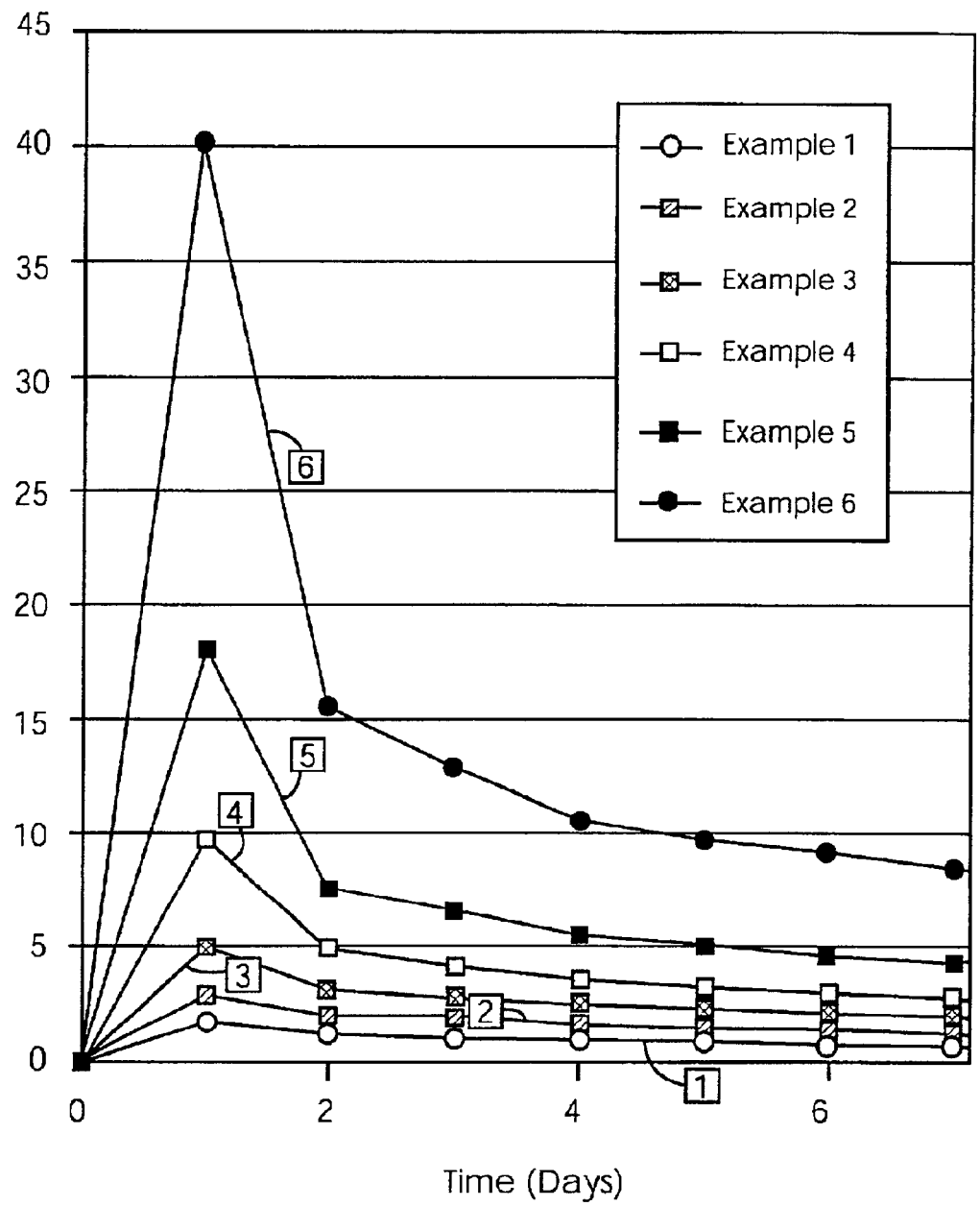
FIG. 1 is a daily release profile illustrating the amount of Metronidazole (mg) released in vitro each day over a seven day period for the intravaginal antimicrobial rings of Examples 1–6.

The present invention primarily concerns itself with intravaginal delivery of antimicrobial agents, including microstatic agents and/or microcidal agents, for the treatment or prevention of vaginitis, although by no means is limited thereto.

Other microbial infections to affect the female genital tract include fungal infections such as vaginal candidiasis, viral herpes genitalis and human papilloma virus—the present invention also concerns itself therewith.

The term "microstatic agent" is intended to embrace any antimicrobial agent which, in use, prevents an increase in the number of susceptible pathogenic organisms. The term "microcidal agent" is intended to embrace any antimicrobial agent which, in use, results in a clinically significant reduction in the number of susceptible pathogenic organisms. The terms "microstatically effective" and "microcidally effective" are analogously intended to embrace effective to prevent an increase in the number of susceptible pathogenic organisms or effective to result in a clinically identifiable reduction in the number of susceptible pathogenic organisms, respectively. A therapeutically effective amount of antimicrobial agent is that which is microstatically effective and/or microcidally effective.

The term "antimicrobial agent" is intended to embrace antibacterial agents, antifungal agents, antiprotozoal agents, antiviral agents and mixtures thereof.

Suitable antibacterial agents include Acrosoxacin, Amifloxacin, Amoxycillin, Ampicillin, Aspoxicillin, Azidocillin, Azithromycin, Aztreonam, Balofloxacin, Benzylpenicillin, Biapenem, Brodimoprim, Cefaclor, Cefadroxil, Cefatrizine, Cefcapene, Cefdinir, Cefetamet, Cefmetazole, Cefprozil, Cefroxadine, Ceftibuten, Cefuroxime, Cephalexin, Cephalonium, Cephaloridine, Cephamandole, Cephazolin,Cephradine, Chlorquinaldol, Chlortetracycline, Ciclacillin, Cinoxacin, Ciprofloxacin, Clarithromycin, Clavulanic Acid, Clindamycin, Clofazimine, Cloxacillin, Danofloxacin, Dapsone, Demeclocycline, Dicloxacillin, Difloxacin, Doxycycline, Enoxacin, Enrofloxacin, Erythromycin, Fleroxacin, Flomoxef, Flucloxacillin, Flumequine, Fosfomycin, Isoniazid, Levofloxacin, Mandelic Acid, Mecillinam, Metronidazole, Minocycline, Mupirocin, Nadifloxacin, Nalidixic Acid, Nifuirtoinol, Nitrofurantoin, Nitroxoline, Norfloxacin, Ofloxacin, Oxytetracycline, Panipenem, Pefloxacin, Phenoxymethylpenicillin, Pipemidic Acid, Piromidic Acid, Pivampicillin, Pivmecillinam, Prulifloxacin, Rufloxacin, Sparfloxacin, Sulbactam, Sulfabenzamide, Sulfacytine, Sulfametopyrazine, Sulphacetamide, Sulphadiazine, Sulphadimidine, Sulphamethizole, Sulphamethoxazole, Sulphanilamide, Sulphasomidine, Sulphathiazole, Temafloxacin, Tetracycline, Tetroxoprim, Tinidazole, Tosufloxacin, Trimethoprim and salts or esters thereof.

Preferred antibacterial agents include tetracyclines such as Doxycycline, Tetracycline or Minocycline; macrolides such as Azithromycin, Clarithromycin and Erythromycin; nitroimidazoles such as Metronidazole or Tinidazole; quinolones such as Ofloxacin, Norfloxacin, Cinoxacin, Ciprofloxacin and Levofloxacin; Clindamycin and Dapsone.

Suitable antifungal agents include Bifonazole, Butoconazole, Chlordantoin, Chlorphenesin, Ciclopirox Olamine, Clotrimazole, Eberconazole, Econazole, Fluconazole, Flutrimazole, Isoconazole, Itraconazole, Ketoconazole, Miconazole, Nifuroxime, Tioconazole, Terconazole, Undecenoic Acid and salts or esters thereof.

Preferred antifungal agents include Clotrimazole, Econazole, Fluconazole, Itraconazole, Ketoconazole, Miconazole, Terconazole and Tioconazole.

Suitable antiprotozoal agents include Acetarsol, Azanidazole, Chloroquine, Metronidazole, Nifuratel, Nimorazole, Omidazole, Propenidazole, Secnidazole, Sineflngin, Tenonitrozole, Temidazole, Tinidazole and salts or esters thereof.

Metronidazole, Tinidazole and Chloroquine are most preferred antiprotozoal agents.

Suitable antiviral agents include Acyclovir, Brivudine, Cidofovir, Curcumin, Desciclovir, 1-Docosanol, Edoxudine, Fameyclovir, Fiacitabine, Ibacitabine, Imiquimod, Lamivudine, Penciclovir, Valacyclovir, Valganciclovir and salts or esters thereof.

Curcumin, Acyclovir, Famcyclovir and Valacyclovir are preferred antiviral agents.

The most preferred antimicrobial agents of this invention include, without limitation, Metronidazole, Acyclovir, Clotrimazole, Fluconazole, Terconazole, Azithromycin, Erythromycin, Doxycycline, Tetracycline, Minocycline, Clindamycin, Famcyclovir, Valacyclovir, Clarithromycin, a prodrug or salt thereof and combinations thereof.

Mixtures of antibacterial agents, mixtures of antifungal agents; mixtures of antiviral agents; mixtures of antiprotozoal agents and mixtures of agents from two or more of these categories are also envisaged by the present invention. In addition, it is also envisaged that the present invention embraces at least one antimicrobial agent (microstatic and/or microcidal agent) with one or more other pharmaceutically active agent.

The antimicrobial agent is generally present in the device of this invention in an amount from about 0.5 to about 80 w/w % and preferably from about 10 to about 70 w/w % of the device. However, the amount of antimicrobial agent may clearly be varied depending on, for example, the desired dosing level, the particular antimicrobial agent, the release rate effect of excipients used in the device, and the particular elastomeric system employed.

The term "elastomer" is intended to mean an amorphous high polymer (or mixture thereof) above its/their glass transition temperature. Elastomers can be stretched and retracted rapidly; exhibit high strength and modulus when stretched; and recover fully when the stress is removed. The term "elastomer" includes covalently-linked elastomers, in which the polymer(s) is/are permanently crosslinked to restrain gross mobility, and thermoplastic elastomers, in which the polymer(s) is/are reversibly crosslinked to restrain gross mobility.

The term "hydrophobic" is intended to describe a polymer that is more soluble in organic solvent than water in a hydrophilic solvent such as water.

Examples of suitable biocompatible elastomers include, but are not limited to, silicones (organo polysiloxanes including dimethylpolysiloxanes), polyethylene-co-poly (vinyl acetate), styrene-butadiene-styrene block copolymers, polyphosphazenes, poly(isoprene), poly (isobutylene), polybutadienes, polyurethanes, nitrile rubbers, neoprene rubbers or mixtures thereof. Silicones are particularly preferred.

More preferred elastomers include hydroxyl-terminated organopolysiloxanes (such as polydimethylsiloxanes) of the RTV (room temperature vulcanising) type, which harden to elastomers at room temperature or higher, following the addition of cross-linking agents (such as alkylorthosilicates, preferably n-propyl or ethyl orthosilicate) in the presence of curing catalysts. Suitable cross-linking agents and curing catalysts are well known in the art. A typical curing catalyst would be stannous octoate. Curing temperatures and times will vary, depending on the particular elastomer(s) used. For example, the curing temperature may vary between room temperature (15–25° C.) and 150° C. but is preferably within the range 60–100° C. The curing time may vary between a few seconds and several hours, depending on the elastomer(s) used.

Other preferred and suitable elastomers include two-component dimethylpolysiloxane compositions using platinum as the curing catalyst and at a curing temperature of from room temperature to an elevated temperature.

Said intravaginal elastomer drug delivery device may have any shape and be of any dimensions compatible with intravaginal administration to the human female or other animal. With the requirements imposed by drug delivery kinetics, a particularly preferred intravaginal drug delivery device according to the present invention is a ring. Such a ring can be self-inserted high into the vagina, where it is held in place due to its shape and inherent elasticity. More preferred is a drug delivery device in the form of a ring, in which the elastomer is silicone.

Such an intravaginal elastomer drug delivery device permits single intravaginal dosing of an antimicrobial agent(s), with an initially high "loading" and a subsequent, lower "maintenance" release profile. In addition, such a device provides high patient compliance, ease of application and exhibits no leakage or messiness on insertion and subsequent placement within the vaginal space.

Preferred antimicrobial agents include quinolones, macrolides, clindamycin, tetracyclines, antibacterial and antifungal agents such as nitroimidazoles and antiviral agents such as acyclovir, a pro-form thereof or a salt thereof. More preferably, the antimicrobial agent is a nitroimidazole such as metronidazole, a pro-form thereof or a salt thereof. A pro-form (or pro-drug) means a precursor which, in vivo, is broken down to release the active agent. Most preferably, the intravaginal drug delivery device is capable of releasing metronidazole, a pro-form thereof or a salt thereof. The intravaginal drug delivery device is capable of releasing an antimicrobial agent into, in use, the vaginal space, at an initial release rate of 1–600 mg, preferably 1–500 mg, most preferably 1–250 mg, of at least one antimicrobial agent, most preferably 1–250 mg of metronidazole, as determined in vitro, over a first day followed by a "maintenance" release rate of 0.25–400 mg, preferably 0.25–300 mg, most preferably 0.25–100 mg, of at least one antimicrobial agent, most preferably 0.5–100 mg of metronidazole as determined in vitro, on a daily basis for at least the following three day period, so that, in use, there is at least no clinically significant increase in the number of viable colony forming units of susceptible pathogenic micro-organisms within the vaginal space.

In a preferred embodiment, the antimicrobial agent should have a solubility in distilled water of not less than 1 $\mu$g per 100 ml, more preferably not less than 100 $\mu$g per 100 ml, still more preferably not less than 1 mg per 100 ml, most preferably not less than 10 mg per 100 ml, at 20° C. Such hydrophilicity is desired to ensure an adequate level of the antimicrobial agent in the space between the device and the vaginal epithelium, hereinafter referred to as the "vaginal space". While not necessary, one, or each, antimicrobial agent generally will have a lipid solubility in liquid silicone at 37° C. of not less than 0.01 mg per 100 ml, optionally not less than 0.1 mg per 100 ml. Such lipophilicity may be desirable to ensure adequate diffusion of the one, or each, antimicrobial agent throughout the matrix of the device.

While the description hereunder mainly concerns metronidazole, which is a preferred antibacterial and/or antiprotozoal agent, it is not intended that the description be limited thereto. Metronidazole, a synthetic 5-nitroimidazole (2-methyl-5-nitro-1H-imidazole-1-ethanol), has antimicrobial action against anaerobic bacteria (e.g., *Gardnerella vaginalis, Bacteroides fragilis, Clostridia* species, *Fusobacteria* species, *Peptococci* and *Peptostreptococci* species), and protozoals (e.g., *Giardia lamblia, Entameba hystolytica, Trichomonas vaginalis*) and is of clinical value in the treatment of trichomoniasis and bacterial vaginosis.

Prejudice against the incorporation of antimicrobial agents such as metronidazole, a pro-drug or a salt thereof, in particular, in an intravaginal elastomer drug delivery device, for the treatment of vaginitis of susceptible bacterial or protozoal origins in the human female is due to:

a) The high water solubility of metronidazole compared to known permeants through cured hydrophobic silicone elastomer. Thus, metronidazole has a solubility in water at 20° C. of 1 g per 100 ml (Merck Index, 11$^{th}$ Edition p. 6079, 1989) compared to norethisterone acetate with an aqueous solubility of less than 10 mg per 100 ml between 15° C.–25° C. and oestradiol-3-acetate, which has an aqueous solubility of only 190 $\mu$g per 100 ml at 37° C.

b) The low solubility of metronidazole in a hydrophobic environment. Silicone oil solubility is an acknowledged measure of solubility in a cured hydrophobic silicone system (Chien, Y., Novel Drug Delivery Systems, 2$^{nd}$ edition, Marcel Dekker, New York, 1992). Metronidazole has a solubility in silicone oil of only 0.6 mg per 100 ml, compared to known efficient permeants through cured silicone, for example, norethisterone acetate and oestradiol-3-acetate, which have a silicone oil solubility of 0.655 g per 100 ml and of 0.237 g per 100 ml, respectively, both determined by experimental solubility determinations at 37° C., by methods known to those skilled in the art.

Despite its unpromising water and oil solubilities, it has now been found possible to deliver microstatically and/or microcidally effective quantities of metronidazole, a pro-drug or a salt thereof, from an elastomeric intravaginal drug delivery device of matrix design.

Preferably, said device is capable of releasing between 5 and 250 mg, more preferably between 9 and 150 mg, of at least one antimicrobial agent, most preferably between 9 and 150 mg of metronidazole, a pro-drug or a salt thereof over the first day, as determined in vitro.

More preferably, said device is capable of releasing at least one antimicrobial agent, at a mean daily rate, following the initial 24 hour period, of between 3 and 175 mg, preferably between 3 and 75 mg of at least one antimicrobial agent, most preferably between 3 and 75 mg of metronidazole, a prodrug or a salt thereof, per day over at least the following three day period, as determined in vitro.

Advantageously, the intravaginal drug delivery device may contain other pharmaceutically compatible agents. Such agents include pharmacologically active agents, as well as, pharmacologically inactive agents known in the art as pharmaceutical excipients. Examples of pharmacologically active agents that may be advantageous include, but are not limited to, a local anaesthetic such as lidocaine or a local analgesic or a mixture thereof. Examples of pharmacologically inactive agents that may be advantageous include, but are not limited to, a buffer (or buffers), or hydrophilic compounds that enhance the rate of release of the agent from the device, such as for example, polyvinylpyrrolidone (PVP or povidone), modified cellulose ethers (e.g., hydroxyethylcellulose, hydroxypropylcellulose and hydroxypropylmethylcellulose) microcrystalline cellulose, polyacrylic acid, carbomer, alginic acid, carrageenan, cyclodextrins, dextrin, guar gum, gelatin, xanthan gum and sugars (e.g., monosaccharides such as glucose, fructose and galactose, and dissaccharides such as lactose, maltose and fructose). When employed, the release rate enhancing excipient is generally present in an amount of about 0.5 to about 40 w/w % and preferably about 2.5 to about 15 w/w % of the device.

According to a second aspect of the invention, there is provided a method of manufacturing an intravaginal drug delivery device according to the first aspect of the present invention, said method comprising the steps of combining and curing an antimicrobial agent or the mixture thereof, and an elastomer, or the mixture thereof, whereby the amount of the agent(s), included in the device is/are selected to provide the desired agent(s) release characteristics.

The amount of antimicrobial agent to be included should be such as to achieve, in use, at least a microstatic effect, i.e., no change in the number of susceptible pathogenic organisms in the vaginal space, but preferably a microcidal effect, i.e., a dclinically significant reduction in the number of susceptible pathogenic organisms in the vaginal space. Similarly, the terms "bacteriostatic" and "bacteriocidal" mean no change, and a clinically significant reduction, respectively, in the number of susceptible pathogenic bacteria in the vaginal space following insertion of the device into the vaginal space.

A drug loading of at least 0.64% (w/w) metronidazole produces a microstatic effect, whereas a drug loading of at least 1.6% (w/w), preferably at least 6.4% (w/w), metronidazole is needed to produce a microcidal effect, in the absence of a release enhancing excipient, as will be evident from Examples 1–6 hereunder. When a release enhancing excipient is present, and this is preferred, lower drug loadings can achieve the same microstatic or microcidal effects, as will be evident from Examples 7 and 8 hereunder.

Although a matrix device shows first order release decay, the "maintenance" rate of drug release, following the initial 24 hour period, can be adapted to "appear" substantially constant if the diffusional distance that the drug must travel from the receding drug boundary to the outer surface of the device is as small as possible. This, in effect, means that the drug loading can be employed to reduce the diffusional distance and, thereby, "simulate" a zero order release over the present required time span, whilst maintaining an initial loading dose over the first 24 hours. The geometry of the ring (where the device is a ring) also plays a role in achieving the desired drug release characteristics—in the present context, the term "igeometry" encompasses the overall diameter of the ring and its cross-sectional diameter.

An initial release rate of at least 1 mg/day of metronidazole, as determined in vitro, produces a microstatic effect in susceptible organisms, whereas an initial release rate of at least 2.5 mg/day, more preferably at least 9 mg/day metronidazole, as determined in vitro is needed to produce a microcidal effect.

A "maintenance" release rate of at least 0.5 mg of metronidazole, per day, over at least the following three days produces a microstatic effect, whereas a "maintenance" release rate of at least 1 mg, preferably at least 3 mg, more preferably at least 4 mg, per day over at least the following three day period, is needed to produce a microcidal effect.

The particle size of the antimicrobial agent may be varied to alter the release rate characteristics of the device of this invention. Generally, the antimicrobial agent used in the present invention will have a particle size distribution wherein 90% have a particle size of less than 200 $\mu$m and 50% have a particle size of less than 50 $\mu$m, preferably 90% have a particle size less than 150 $\mu$m, and 50% have a particle size less than 30 $\mu$m and most preferably 90% have a particle size less than 90 $\mu$m and 50% have a particle size less than 20 $\mu$m.

Several embodiments of the invention will now be described by reference to the following examples. It should be understood that these examples are disclosed solely by way of further illustrating the invention and should not be taken in any way to limit the scope of said invention.

GENERAL METHOD OF MANUFACTURE

Examples 1 to 8

An intravaginal drug delivery device according to the present invention was prepared by blending 100 parts by weight of a hydrophobic elastomeric polymer (polydimethylsiloxane) containing about 25% w/w diatomaceous earth as the filler, with 2.5 parts by weight of a cross-linking agent, n-propylorthosilicate, to form an elastomer mix. One suitable hydrophobic elastomeric polymer is stannous octoate-cured polydimethylsiloxane polymer, a suitable example of which is Dow Corning 382. The appropriate amount of metronidazole, previously sieved to a particle size of less than 180 micrometres, was then added. The amount of metronidazole added to the elastomer mix varied between 0.64 and 25.6% (w/w), as required, per weight of final manufactured device. Optionally, additional pharmacologically active agents or pharmaceutical excipients can be included at this stage by similarly blending them into the mix. Prior to injection moulding or extrusion, the metronidazole-containing mix was activated by blending 200 parts by weight of this mix with 1 part by weight of a catalyst, for example, stannous octoate. The resultant final active mix is injected into a suitable mould and cured at 80° C. for 2 minutes. The mould is then opened, following which the device is removed and trimmed. The geometric characteristics of the device can be varied as required by the use of appropriately sized moulds or extrusion nozzles, as will be obvious to those skilled in the art.

Examples 1–6

An intravaginal drug delivery device in the form of a matrix design ring having a metronidazole content of 0.64, 1.6, 3.2, 6.4, 12.8, 25.6% (w/w), respectively, was prepared by following the General Method of Manufacture set out hereinabove, with a ring geometry of 7.6 mm (cross-sectional diameter) and 56 mm (outer diameter) to yield the devices of, respectively, Examples 1–6.

The daily release results showing the amount of Metronidazole (mg) released in vitro each day over a 14 day period for the devices of Examples 1–6 are set forth in Table 1 below.

TABLE 1

| Day | 50 mg 0.64% | 125 mg 1.60% | 250 mg 3.20% | 500 mg 6.40% | 1000 mg 12.80% | 2000 mg 25.60% |
| --- | --- | --- | --- | --- | --- | --- |
| 1 | 1.74 | 3.11 | 5.12 | 9.93 | 18.16 | 40.44 |
| 2 | 1.22 | 2.08 | 3.19 | 4.86 | 7.44 | 15.55 |
| 3 | 1.04 | 1.83 | 2.79 | 4.23 | 6.51 | 12.98 |
| 4 | 1.01 | 1.63 | 2.51 | 3.63 | 5.5 | 10.66 |
| 5 | 0.94 | 1.58 | 2.32 | 3.37 | 5.1 | 9.84 |
| 6 | 0.87 | 1.48 | 2.22 | 3.21 | 4.79 | 9.27 |
| 7 | 0.78 | 1.34 | 1.96 | 2.96 | 4.44 | 8.55 |
| 8 | 0.73 | 1.22 | 1.82 | 2.72 | 4.39 | 8.18 |
| 9 | 0.67 | 1.14 | 1.72 | 2.64 | 4.28 | 7.92 |
| 10 | 0.66 | 1.09 | 1.6 | 2.62 | 4.06 | 7.55 |
| 11 | 0.62 | 0.97 | 1.47 | 2.44 | 3.79 | 6.93 |
| 12 | 0.58 | 0.86 | 1.41 | 2.39 | 3.61 | 6.33 |
| 13 | 0.53 | 0.81 | 1.38 | 2.3 | 3.42 | 6.1 |
| 14 | 0.49 | 0.77 | 1.35 | 2.21 | 3.3 | 5.55 |

The release results showing the amount of Metronidazole (mg) cumulatively released over a 14 day period for the devices of Examples 1–6 are set forth in Table 2 below.

TABLE 2

| Day | 50 mg 0.64% | 125 mg 1.60% | 250 mg 3.20% | 500 mg 6.40% | 1000 mg 12.80% | 2000 mg 25.60% |
| --- | --- | --- | --- | --- | --- | --- |
| 1 | 1.74 | 3.11 | 5.12 | 9.93 | 18.16 | 40.44 |
| 2 | 2.96 | 5.19 | 8.31 | 14.80 | 25.60 | 55.99 |

TABLE 2-continued

| Day | 50 mg 0.64% | 125 mg 1.60% | 250 mg 3.20% | 500 mg 6.40% | 1000 mg 12.80% | 2000 mg 25.60% |
|---|---|---|---|---|---|---|
| 3 | 4.00 | 7.03 | 11.10 | 19.03 | 32.11 | 68.97 |
| 4 | 5.01 | 8.66 | 13.61 | 22.66 | 37.61 | 79.63 |
| 5 | 5.95 | 10.24 | 15.93 | 26.02 | 42.71 | 89.47 |
| 6 | 6.82 | 11.72 | 18.15 | 29.23 | 47.49 | 98.74 |
| 7 | 7.59 | 13.06 | 20.10 | 32.20 | 51.93 | 107.29 |
| 8 | 8.33 | 14.27 | 21.93 | 34.91 | 56.32 | 115.47 |
| 9 | 9.00 | 15.42 | 23.65 | 37.55 | 60.60 | 123.39 |
| 10 | 9.65 | 16.51 | 25.25 | 40.17 | 64.66 | 130.93 |
| 11 | 10.27 | 17.48 | 26.72 | 42.61 | 68.45 | 137.86 |
| 12 | 10.85 | 18.34 | 28.13 | 45.00 | 72.06 | 144.18 |
| 13 | 11.38 | 19.14 | 29.51 | 47.30 | 75.48 | 150.28 |
| 14 | 11.87 | 19.91 | 30.86 | 49.51 | 78.78 | 155.83 |

Examples 7 and 8

An intravaginal drug delivery device in the form of a matrix design ring having a metronidazole content of 0.64% (w/w) and a povidone (PVP) content of 5% or 10%, respectively, by weight was prepared by following the General Method of Manufacture set out hereinabove, with a ring geometry of 7.6 mm (cross-sectional diameter) and 56 mm (outer diameter), to yield the devices of, respectively, Examples 7 and 8.

Example 7a

An intravaginal drug delivery device in the form of a matrix design ring having a metronidazole content of 1.28% (w/w) was prepared by following the General Method of Manufacture set out hereinabove, with a ring geometry of 7.6 mm (cross-sectional diameter) and 56 mm (outer diameter), to yield the device of Example 7a.

The release results showing the amount of Metronidazole (mg) cumulatively released over a 21 day period for the devices of Examples 1, 7, 7a and 8, are set forth in Table 3 below.

TABLE 3

| Day | 50 mg MET | 100 mg MET | 50 mg MET plus 5% PVP | 50 mg MET plus 10% PVP |
|---|---|---|---|---|
| 1 | 2.73 | 3.77 | 3.54 | 5.25 |
| 2 | 4.56 | 6.38 | 5.38 | 7.40 |
| 3 | 6.07 | 8.47 | 6.97 | 9.23 |
| 6 | 8.96 | 12.40 | 9.76 | 12.02 |
| 7 | 9.93 | 13.80 | 10.79 | 13.09 |
| 8 | 10.84 | 15.02 | 11.69 | 13.96 |
| 13 | 14.52 | 20.38 | 15.44 | 17.71 |
| 14 | 15.11 | 21.17 | 16.19 | 18.42 |
| 21 | 18.66 | 26.02 | 19.32 | 22.04 |

IN VITRO DRUG RELEASE

Examples 1 to 8

Figure 2:
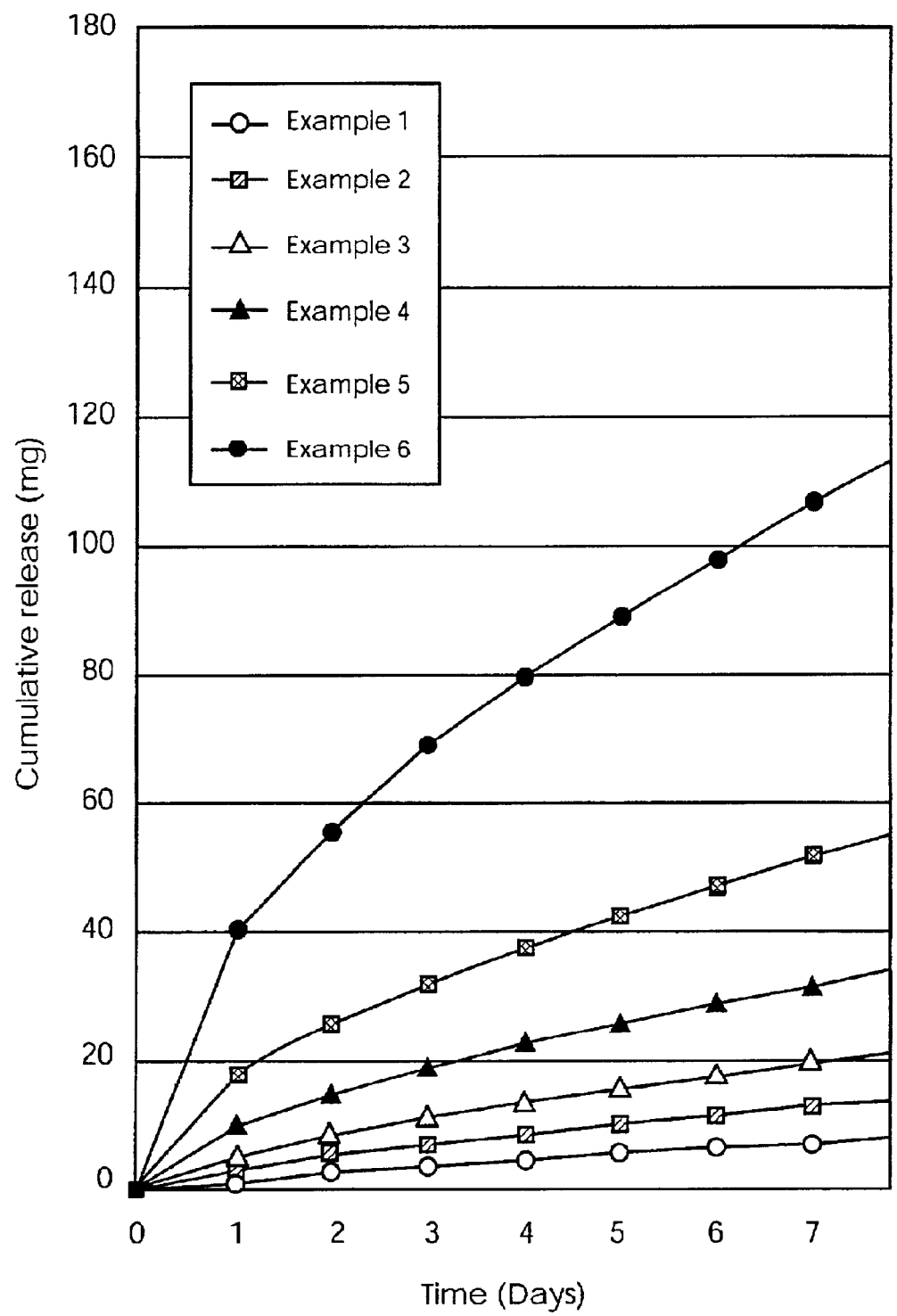
FIG. 2 is a cumulative release profile illustrating the total amount of Metronidazole (mg) released in vitro over time for the intravaginal antimicrobial rings of Examples 1–6.
Figure 3:
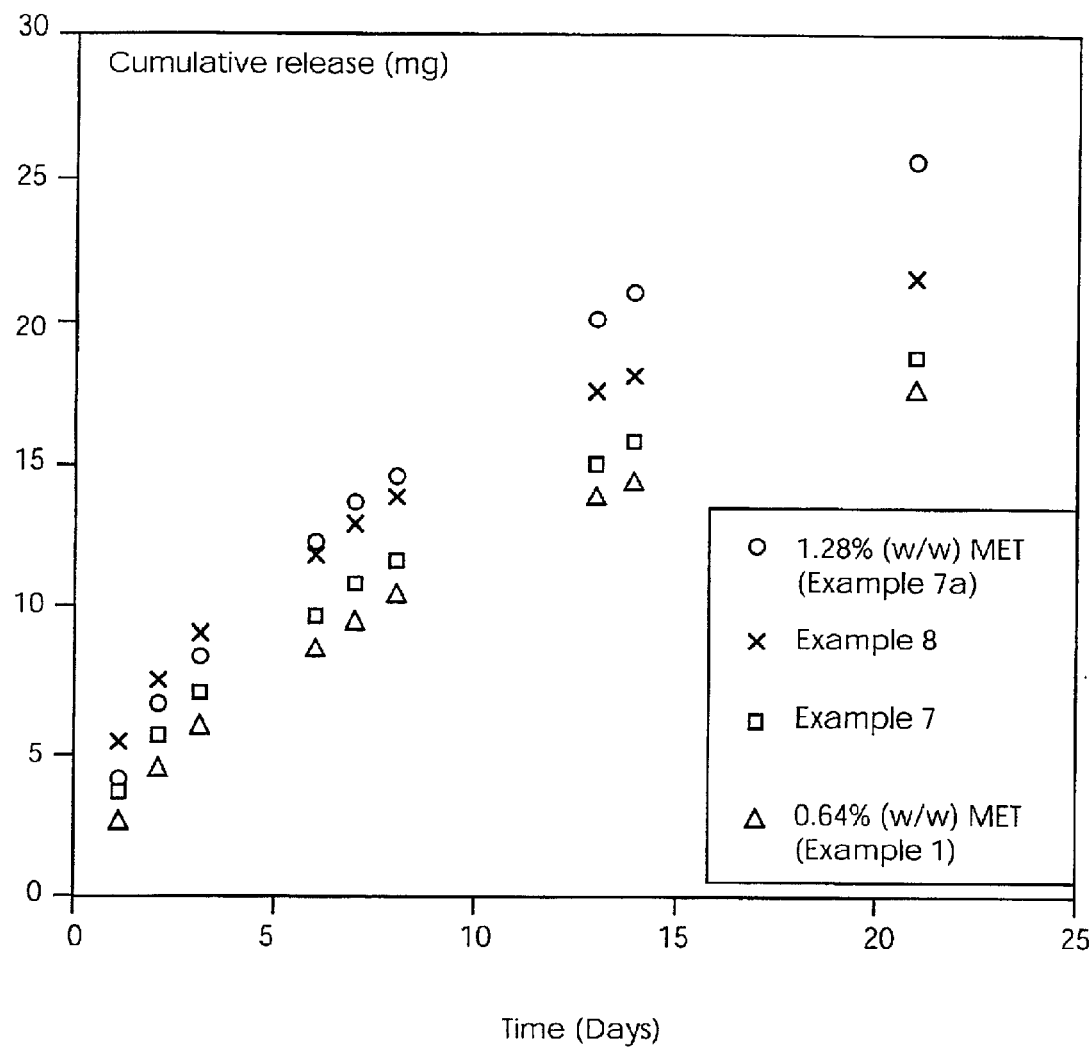

The in vitro daily release and cumulative profiles set out in FIGS. 1 and 2 for the rings of Examples 1–6 and the cumulative profiles in FIG. 3 for the rings of Examples 1, 7, 7a and 8 were determined under sink conditions in pH 5.0 phosphate buffer. The term 'sink conditions' refers to that set of experimental conditions in vitro that effectively simulates the active haemoperfusion that occurs in vivo, and which results in a maximum drug diffusion rate, at any given time, across the aqueous boundary layer. Release rates were determined in the following manner.

Each intravaginal ring (n=4) was suspended in the dissolution medium in an individual 250 ml flask which is then capped. The flasks were maintained at a constant temperature of 37° C. in a shaking incubator. The contents of each flask were gently shaken at a constant rate (100 rotations per minute) selected to ensure the absence of a hydrostatic layer on the surface of the ring. The dissolution medium was renewed every 24 hours (±15 minutes) over a 7–21 day period. An aliquot (1 ml) of the used dissolution medium was analysed by high performance liquid chromatography.

The daily release profiles, over 7 days, of metronidazole from the devices of Examples 1–6 are shown in FIG. 1, where the amount of drug released daily (mg) is plotted against time (days). The profiles show a relatively large release of metronidazole in the first day, decreasing with time thereafter. Rings containing 25.6% (w/w) of metronidazole exhibited a significantly greater initial release (40.44 mg) in comparison to those containing lower drug loadings, i.e. 12.8% (w/w) to 0.64% (w/w).

A plot of the cumulative amount of drug released (mg) from the matrix devices of Examples 1–6 yields a series of profiles (FIG. 2) that, between day 2 and day 7 approximate a linear pattern (substantially linear or substantially constant). Overall, the total maximum amount of metronidazole released for each ring following a seven day period was: 107.7 mg (Example 6), 53.8 mg (Example 5), 27.7 mg (Example 4), 16.9 mg (Example 3), 12.3 mg (Example 2) and 7.7 mg (Example 1).

A plot of the cumulative amount of drug released (mg) from the matrix devices of Examples 7–8 yields a series of profiles (FIG. 3) that demonstrate the advantage of including a release enhancing excipient (povidone or PVP). For example, it is apparent from FIG. 3 that an intravaginal matrix ring containing 0.64% (w/w) of metronidazole (MET) and 10% PVP (Example 8) by weight produces a similar release profile to that of a similar ring containing 1.28% (w/w) of metronidazole in the absence of the release enhancing excipient (Example 7a), over a seven day period.

Antibacterial Efficacy

The rings of Examples 1–6 were tested for their antibacterial efficacy. Stationary phase *Gardnerella vaginalis* was grown anaerobically in Brain Heart Infusion (BHI) for a period of 48 hours at 37° C. The resulting culture was adjusted to an $OD_{540}$ of 0.1. In order to obtain a bacterial challenge of around $5 \times 10^5$ cfu/ml, 5 ml of this suspension was added to one litre of BHI. The exact viable count of this *Gardnerella vaginalis* challenge was performed using the Miles and Misra drop technique.

Sterile metronidazole intravaginal rings of Examples 1–6, autoclaved for a period of 15 minutes at 120° C. and a pressure of 15 Psi, and control placebo rings containing no metronidazole, were placed in the aforementioned bacterial suspension (100 ml) and incubated at 37° C. in an anaerobic environment. After regular time intervals of up to 24 hours, 1ml samples of the bacterial suspension were removed. The viable count (cfu/ml) was obtained using the Miles and Misra dilution technique in which 6×0.02 ml drops of each serially diluted samples were transferred onto Bartonella agar plates and incubated anaerobically overnight at 37° C. The data obtained is presented in Table 4.

TABLE 4

Number of surviving micro-organisms as a function of incubation time (hours)

| Sample | 0 hour | 1 hour | 2 hours | 3 hours | 4 hours | 24 hours |
|---|---|---|---|---|---|---|
| Placebo | $2.00 \times 10^6$ | $1.60 \times 10^6$ | $2.80 \times 10^6$ | $3.50 \times 10^6$ | $7.50 \times 10^6$ | $1.20 \times 10^9$ |
| Example 1 | $2.00 \times 10^6$ | $2.90 \times 10^6$ | $1.90 \times 10^6$ | $5.00 \times 10^6$ | $6.20 \times 10^6$ | $2.60 \times 10^7$ |
| Example 2 | $2.00 \times 10^6$ | $1.70 \times 10^6$ | $1.30 \times 10^6$ | $3.10 \times 10^6$ | $4.80 \times 10^6$ | $5.80 \times 10^4$ |
| Example 3 | $2.00 \times 10^6$ | $1.90 \times 10^6$ | $1.40 \times 10^6$ | $2.20 \times 10^6$ | $3.40 \times 10^6$ | $3.30 \times 10^4$ |
| Example 4 | $2.00 \times 10^6$ | $6.20 \times 10^5$ | $1.30 \times 10^6$ | $1.60 \times 10^6$ | $1.30 \times 10^6$ | $1.30 \times 10^3$ |
| Example 5 | $2.00 \times 10^6$ | $3.10 \times 10^6$ | $1.10 \times 10^6$ | $8.50 \times 10^5$ | $2.00 \times 10^5$ | 0.00 |
| Example 6 | $2.00 \times 10^6$ | $1.10 \times 10^6$ | $1.30 \times 10^6$ | $1.80 \times 10^5$ | $4.30 \times 10^4$ | 0.00 |

Following a three hour incubation period, a greater bactericidal effect against *Gardnerella vaginalis* was observed for rings of Examples 5 and 6, containing 12.8% (w/w) and 25.6% (w/w) of metronidazole, respectively. The bactericidal effect of rings of Examples 3–6 was even more apparent following their incubation with *Gardnerella vaginalis* for a period of four hours. Within this period, the number of surviving *Gardnerella vaginalis* organisms significantly decreased in the presence of 25.6% (w/w), 12.8% (w/w), 6.4% (w/w) and 3.2% (w/w)-containing metronidazole rings, in comparison to the placebo devices (Table 4).

An effective bactericidal effect was observed for the rings of Examples 5 and 6 following 24 hours incubation with *Gardnerella vaginalis*. In addition, significantly lower numbers of surviving organisms were found in the presence of rings of Examples 2–4, in comparison to placebo rings.

Intravaginal elastomeric rings of the present invention have the ability to both inhibit and kill *Gardnerella vaginalis*, the primary causative organism of bacterial vaginosis, by release of metronidazole over a 24 h period. The ring of Example 2 is the lowest concentration providing a bactericidal effect but all rings of Examples 1–6 show bacteriostatic activity. Substantial bacteriocidal activity is exhibited (99.9%) over 24 hours with the rings of Examples 4–6.

GENERAL METHOD OF MANUFACTURE

Examples 9 to 11

An intravaginal drug delivery device in the form of a matrix design ring was prepared by blending 97 parts by weight of a hydrophobic elastomeric polymer (polydimethylsiloxane) containing about 25% w/w diatomaceous earth as the filler, with 2.5 parts by weight of a cross-linking agent, n-propylorthosilicate, to form an elastomer mix. One suitable hydrophobic elastomeric polymer is stannous octoate-cured polydimethylsiloxane polymer, a suitable example of which is Dow Corning 382. At this stage, elastomeric polymer, containing no filler, and additional cross-linker are added to reduce the final concentration of filler in the elastomer mix. Metronidazole was added to the elastomer mix described above to form an active mix with a drug content up to 50% (w/w). Optionally, additional pharmacologically-active agents or pharmaceutical excipients can be included at this stage by similarly blending them into the active mix. Prior to injection moulding, the active mix was activated by blending 100 to 150 parts by weight of elastomer in the active mix with 1 part by weight of an activating catalyst e.g. stannous octoate. The resultant final active mix was injected into a suitable mould for a matrix design ring and cured at 80° C. for 2 minutes or at room temperature for up to 1 hour. The mould is opened, following which the ring is removed. The geometric characteristics of the ring can be varied as required by the use of appropriately sized moulds as described hereinbefore.

IN VITRO DRUG RELEASE

Examples 9 to 11

Each ring was suspended in a flask containing 250 ml saline (0.9% (w/v) NaCl) and the flask capped. The flask was placed in an orbital shaker maintained at 37° C. and shaken at a speed of 80 rpm. The dissolution medium was renewed every 24 hours. An aliquot (1 ml) of the used dissolution medium was analysed by HPLC to determine the total daily amount of metronidazole released by each ring.

Examples 9 and 10

An intravaginal drug delivery device in the form of a matrix design ring and containing 40% (w/w) or 35% (w/w) metronidazole, respectively was prepared by following the General Method of Manufacture set out hereinabove, with a ring geometry of 7.6 mm (cross-sectional diameter), 56 mm (outer diameter), by curing an elastomer mix (containing 20% (w/w) diatomaceous earth) at 80° C. for 2 minutes.

Typical in vitro release rates are shown below:

| Day | Example 9 (40%) Mean Drug Release Rate (mg/day) | Example 10 (35%) Mean Drug Release Rate (mg/day) |
|---|---|---|
| 1 | 72 | 48 |
| 2 | 38 | 26 |
| 3 | 29 | 21 |
| 4 | 24 | 17 |
| 5 | 20 | 14 |

Example 11

An intravaginal drug delivery device in the form of a matrix design ring was prepared, with a ring geometry of 7.6 mm (cross-sectional) diameter), 56 mm (outer diameter), by curing an elastomer mix (containing 10% (w/w) diatomaceous earth) at room temperature for 30 minutes. The ring contained 50% (w/w) metronidazole.

Typical in vitro release rates are shown below:

| Day | Mean Drug Release Rate (mg/day) |
|---|---|
| 1 | 109 |
| 2 | 47 |
| 3 | 34 |
| 4 | 29 |

Example 12

Figure 4:
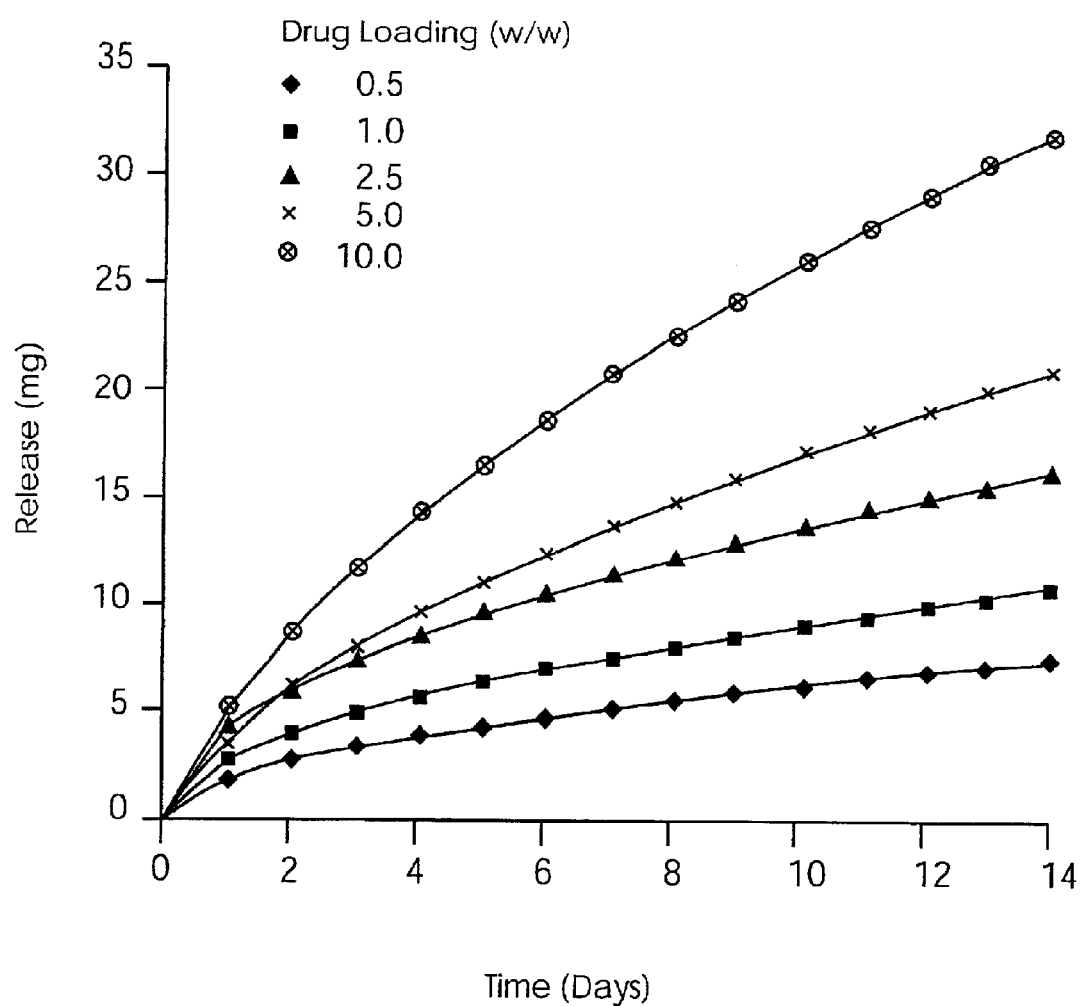
FIG. 4 is a cumulative release profile illustrating the total amount of curcumin (mg) released in vitro over time for Example 12.

Curcumin matrix rings containing various drug (curcumin) loadings (approx. 0.5% (w/w), 1.0% (w/w), 2.5% (w/w), 5.0% (w/w) and 10.0% (w/w)) were manufactured by injection moulding according to the following general method. A standard silicone elastomer mix was prepared by mixing together 51.2 g tetrapropylsilane and 2048.8 g silicone base. The base consisted of a mixture of high and low molecular weight hydroxy-terminated silicones (MW 10,000 and 2,000, respectively) and a silica reinforcing filler. The required amount of curcumin was added to, and intimately mixed with, 30.0 g of the silicone mix. 0.5% (w/w) of stannous octoate was then added, mixed for thirty seconds and injected into the moulds. The injection mixes were cured at 80° C. for two minutes producing elastomer silicone rings weighing about 10.2 g and having the following dimensions: 7.5 mm cross-sectional diameter, 43.0 mm internal diameter, 58.0 mm external diameter. Release was performed into 100 ml of 1% benzalkonium chloride solution and assayed by reverse-phase HPLC. FIG. 4 shows cumulative release (Q in mg) against time (T in days). The cumulative release results (Q in mg) over a 14 day period are set forth in Table 5 below.

TABLE 5

| Day | 0.5% | 1.0% | 2.5% | 5.0% | 10.0% |
|---|---|---|---|---|---|
| 1 | 1.896 | 2.37 | 4.266 | 3.318 | 4.74 |
| 2 | 2.844 | 3.792 | 6.162 | 5.688 | 8.532 |
| 3 | 3.318 | 4.74 | 7.584 | 8.058 | 11.85 |
| 4 | 3.792 | 5.688 | 8.532 | 9.48 | 14.22 |
| 5 | 4.266 | 6.162 | 9.48 | 10.902 | 16.59 |
| 6 | 4.74 | 6.636 | 10.428 | 12.324 | 18.486 |
| 7 | 5.214 | 7.584 | 11.376 | 13.746 | 20.856 |
| 8 | 5.688 | 8.058 | 12.324 | 14.694 | 22.752 |
| 9 | 5.688 | 8.532 | 12.798 | 16.116 | 24.174 |
| 10 | 6.162 | 9.006 | 13.746 | 17.064 | 26.07 |
| 11 | 6.636 | 9.48 | 14.22 | 18.012 | 27.492 |
| 12 | 7.11 | 9.954 | 15.168 | 18.96 | 28.914 |
| 13 | 7.11 | 10.428 | 15.642 | 19.908 | 30.336 |
| 14 | 7.584 | 10.902 | 16.116 | 20.856 | 31.758 |

IN VITRO DRUG RELEASE

Example 13

These release rates were determined in 0.9% (w/v) saline. Each ring (n=6) was suspended in saline, in a volume of 500 ml for day 1 and in 250 ml for each of the subsequent days. The flasks were maintained at 37° C. in a shaking incubator, the saline being refreshed every 24 hours.

IN VITRO DRUG RELEASE

Examples 14 to 17

These release rates were determined in 0.9% (w/v) saline or sodium lauryl sulphate (for Examples 15 and 17). The ring (n=1) was suspended in saline, in a volume of 500 ml for day 1 and in 250 ml for each of the subsequent days. The flasks were maintained at 37° C. in a shaking incubator, the saline being refreshed every 24 hours.

Example 13

An intravaginal drug delivery device according to the present invention was prepared by blending 94.24 parts by weight of a hydrophobic elastomeric polymer (polydimethylsiloxane) containing about 10% w/w diatomaceous earth as the filler, with 5.76 parts by weight of a cross-linking agent, n-propylorthosilicate, to form an elastomer mix. The amount of metronidazole, with a particle size distribution in which 90% is less than 90 Am and 50% is less than 20 μm, added to the elastomer mix was 40% w/w, per weight of final manufactured device. Prior to injection moulding or extrusion, the metronidazole-containing mix was activated by blending 140 parts by weight of this mix with 1 part by weight of a catalyst, for example, stannous octoate. The resultant final active mix was injected into a suitable mould (having a cross-sectional diameter of 9.5 mm and an outer diameter of 54 mm) and cured at 90° C. for 4 minutes. The mould was then opened, following which the device was removed and trimmed. The intravaginal drug delivery device was in the form of a matrix design ring with a ring geometry of 9.2 mm (cross-sectional diameter) and 54 mm (outer diameter). The ring can be subjected to a post curing step at 60° C. for 16 hours, followed by subsequent storage at a temperature of 25° C. and a relative humidity of 60% to improve the mechanical and release characteristics.

Typical in vitro release rates are shown below both for a ring with no post curing (n=6); for a ring with post curing at 60° C. for 16 hours (n=12); and for a ring (n=3) with post curing at 60° C. for 16 hours followed by storage in individual pouches at a controlled temperature (25° C., 60% relative humidity) for 3 weeks:

| | Mean (S.D.) Drug Release Rate (mg/day) | | |
|---|---|---|---|
| Day | No Post Curing | Post Cured at 60° C. 116 hrs | Post Cured at 60° C./16 hrs and stored at the controlled temp. for 3 wks |
| 1 | 82.9 (3.3) | 74.4 (2.5) | 70.5 (0.3) |
| 2 | 42.0 (1.0) | 42.3 (1.6) | 48.6 (1.1) |
| 3 | 31.5 (1.0) | 33.6 (1.3) | 37.2 (0.6) |
| 4 | 24.2 (0.7) | 28.5 (1.1) | 33.1 (1.2) |
| 5 | 21.2 (1.2) | 24.4 (0.8) | 30.1 (0.5) |

Example 14

Acyclovir

An intravaginal drug delivery device according to the present invention was prepared by blending 94.24 parts by weight of a hydrophobic elastomeric polymer (polydimethylsiloxane) containing about 10% w/w diatomaceous earth as the filler, with 5.76 parts by weight of a cross-linking agent, n-propylorthosilicate, to form an elastomer mix. The amount of acyclovir added to the elastomer mix was 20% w/w, per weight of final manufactured device. Additionally, 10% w/w lactose, a water soluble excipient, was added to aid drug release. Prior to injection moulding or extrusion, the acyclovir-containing mix was activated by blending 150 parts by weight of this mix with 1 part by weight of a catalyst, for example, stannous octoate. The resultant final active mix was injected into a suitable mould (having a cross-sectional diameter of 9.5 mm and an outer diameter of 54 mm) and cured at 80° C. for 2 minutes. The mould was then opened, following which the device was removed and trimmed. The intravaginal drug delivery device was in the form of a matrix design ring with a ring geometry of 9.2 mm (cross-sectional diameter) and 54 mm (outer diameter).

Typical in vitro release rates, within 1 week of manufacture, into 0.9% (w/v) saline are shown below:

| Day | Mean (S.D.) Drug Release Rate (ug/day) |
| --- | --- |
| 1 | 5076.0 |
| 2 | 1202.5 |
| 3 | 819.2 |
| 4 | 570.7 |
| 5 | 530.7 |
| 6 | 373.7 |
| 7 | 333.7 |
| 8 | 304.2 |
| 9 | 276.2 |
| 10 | 229.1 |
| 11 | 241.3 |
| 12 | 225.7 |
| 13 | 228.6 |
| 14 | 195.1 |

Example 15

Clotrimazole

An intravaginal drug delivery device according to the present invention was prepared by blending 97 parts by weight of a hydrophobic elastomeric polymer (polydimethylsiloxane) containing about 20% w/w diatomaceous earth as the filler, with 2.5 parts by weight of a cross-linking agent, n-propylorthosilicate, to form an elastomer mix. The amount of clotrimazole added to the elastomer mix was 10% w/w, per weight of final manufactured device. Optionally, additional pharmacologically active agents or pharmaceutical excipients can be included at this stage by similarly blending them into the mix. Prior to injection moulding or extrusion, the clotrimazole-containing mix was activated by blending 200 parts by weight of this mix with 1 part by weight of a catalyst, for example, stannous octoate. The resultant final active mix was injected into a suitable mould (having a cross-sectional diameter of 9.5 mm and an outer diameter of 54 mm) and cured at 80° C. for 2 minutes. The mould was then opened, following which the device was removed and trimmed. The intravaginal drug delivery device was in the form of a matrix design ring with a ring geometry of 9.2 mm (cross-sectional diameter) and 54 mm (outer diameter).

Typical in vitro release rates into 0.3% (w/v) sodium lauryl sulphate, within 6 months of manufacture, are shown below:

| Day | Mean (S.D.) Drug Release Rate (mg/day) |
| --- | --- |
| 1 | 29.1 |
| 2 | 13.2 |
| 3 | 11.3 |
| 4 | 9.7 |
| 5 | 9.6 |
| 6 | 10.0 |
| 9 | 9.8 |

Example 16

Doxycycline

An intravaginal drug delivery device according to the present invention was prepared by blending 94.24 parts by weight of a hydrophobic elastomeric polymer (polydimethylsiloxane) containing about 10% w/w diatomaceous earth as the filler, with 5.76 parts by weight of a cross-linking agent, n-propylorthosilicate, to form an elastomer mix. The amount of doxycycline added to the elastomer mix was 40% w/w, per weight of final manufactured device. Optionally, additional pharmacologically active agents or pharmaceutical excipients can be included at this stage by similarly blending them into the mix. Prior to injection moulding or extrusion, the doxycycline-containing mix was activated by blending 150 parts by weight of this mix with 1 part weight of a catalyst, for example, stannous octoate. The resultant final active mix was injected into a suitable mould (having a cross-sectional diameter of 9.5 mm and an outer diameter of 54 mm) and cured at 80° C. for 2 minutes. The mould was then opened, following which the device was removed and trimmed. The intravaginal drug delivery device was in the form of a matrix design ring with a ring geometry of 9.2 mm (cross-sectional diameter) and 54 mm (outer diameter).

Typical in vitro release rates, within 1 week of manufacture, into 0.9% (w/v) saline are shown below:

| Day | Mean (S.D.) Drug Release Rate (mg/day) |
| --- | --- |
| 1 | 10.3 |
| 2 | 7.3 |
| 3 | 4.8 |
| 4 | 4.8 |
| 5 | 4.1 |
| 6 | 3.9 |
| 7 | 3.9 |
| 8 | 4.0 |
| 9 | 4.1 |
| 10 | 3.3 |
| 11 | 2.9 |
| 12 | 3.2 |
| 13 | 3.4 |
| 14 | 3.2 |
| 15 | 3.3 |
| 16 | 3.3 |

Example 17

Erythromycin

An intravaginal drug delivery device according to the present invention was prepared by blending 94.24 parts by weight of a hydrophobic elastomeric polymer (polydimethylsiloxane) containing about 10% w/w diatomaceous earth as the filler, with 5.76 parts by weight of a cross-linking agent, n-propylorthosilicate, to form an elastomer mix. The amount of erythromycin added to the elastomer mix was 20% w/w, per weight of final manufactured device. Additionally, 10% w/w lactose, a water soluble excipient, was added to aid drug release. Prior to injection moulding or extrusion, the erythromycin-containing mix was activated by blending 150 parts by weight of this mix with 1 part by weight of a catalyst, for example, stannous octoate. The resultant final active mix was injected into a suitable mould (having a cross-sectional diameter of 9.5 mm and an outer diameter of 54 mm) and cured at 80° C. for 2 minutes. The mould is then opened and the device is removed and trimmed. The intravaginal drug delivery device is in the form of a matrix design ring with a ring geometry of 9.2 mm (cross-sectional diameter) and 54 mm (outer diameter).

Typical in vitro release rates, within 1 week of manufacture, into 0.3% (w/v) sodium lauryl sulphate, are shown below:

| Day | Mean (S.D.)Drug Release Rate (mg/day) |
| --- | --- |
| 1 | 25.1 |
| 2 | 15.7 |
| 3 | 8.1 |
| 4 | 10.8 |
| 5 | 7.7 |
| 6 | 5.1 |
| 7 | 4.0 |

The invention is not limited to the embodiments described and exemplified herein, which may be modified and amended without departing from the scope of the present invention.

What is claimed is:

1. An intravaginal antimicrobial drug delivery device comprising:
   a therapeutically effective amount of at least one antimicrobial agent dispersed throughout a biocompatible elastomeric system that forms said delivery device,
   wherein between 5 mg and 600 mg of said at least one antimicrobial agent is released during an initial 24 hour period of use, and
   wherein said delivery device consists essentially of a ring.

2. The intravaginal drug delivery device of claim 1, wherein said biocompatible elastomeric system is hydrophobic.

3. The intravaginal drug delivery device of claim 1, wherein said antimicrobial agent is dispersed homogeneously.

4. The intravaginal drug delivery device of claim 1, wherein the ring has a cross-sectional diameter in a range of about 2.5 to about 15 mm.

5. The intravaginal drug delivery device of claim 4, wherein the ring has an outer diameter in a range of about 40 to about 65 mm.

6. The intravaginal drug delivery device of claim 1, wherein said antimicrobial agent is released at a substantially first order release rate during said initial twenty four hour period of use.

7. The intravaginal drug delivery device of claim 6, wherein said antimicrobial agent is released at a substantially zero order release rate over at least a 3 day period of time, after said initial 24 hour period of use.

8. The intravaginal drug delivery device of claim 1, wherein the solubility in distilled water of said antimicrobial agent is not less than 1 µg/100 ml at 20° C.

9. The intravaginal drug delivery device of claim 2, wherein said hydrophobic elastomeric system is a silicone polymer.

10. The intravaginal drug delivery device of claim 1, wherein between 5 mg and 250 mg of said at least one antimicrobial agent is released during said initial 24 hour period of use.

11. The intravaginal drug delivery device of claim 7, wherein between 0.25 mg and 400 mg of said at least one antimicrobial agent is released per day, for at least said 3 days following said initial 24 hour period of use.

12. The intravaginal drug delivery device of claim 1, wherein said antimicrobial agent is selected from the group consisting of Metronidazole, Acyclovir, Clotrimazole, Fluconazole, Terconazole, Azithromycin, Erythromycin, Doxycycline, Tetracycline, Minocycline, Clindamycin, Famcyclovir, Valacyclovir, Clarithromycin, a prodrug or salt thereof and combinations thereof.

13. The intravaginal drug delivery device of claim 1, further comprising one or more other pharmaceutically compatible agents.

14. The intravaginal drug delivery device of claim 13, wherein said one or more pharmaceutically compatible agents are selected from the group consisting of pharmaceutical excipients, pharmacologically active agents and combinations thereof.

15. The intravaginal drug delivery device of claim 14, wherein said pharmaceutical excipients are selected from the group consisting of buffers, polymers, fillers and combinations thereof.

16. The intravaginal drug delivery device of claim 14, wherein said pharmaceutical excipient is selected from the group consisting of polyvinylpyrrolidone, modified cellulose ethers, microcrystalline cellulose, polyacrylic acid, carbomer, alginic acid, carrageenan, cyclodextrins, dextrin, guar gum, gelatin and xanthan gum, monosaccharides and disaccharides.

17. The intravaginal drug delivery device of claim 14, wherein said pharmacologically active agent is selected from the group consisting of local anaesthetics, local analgesics and combinations thereof.

18. The intravaginal drug delivery device of claim 1, wherein a particle size distribution of the antimicrobial agent is 90% particles of less than 200 microns and 50% particles of less than 50 microns.

19. An intravaginal drug delivery device comprising:
   a therapeutically effective amount of Metronidazole, a prodrug or salt thereof, dispersed throughout a biocompatible elastomeric system that forms said drug delivery device,
   wherein between 5 mg and 600 mg of said Metronidazole is released during an initial 24 hour period of use, and
   wherein said delivery device consists essentially of a ring.

20. The intravaginal drug delivery device of claim 19, wherein said biocompatible elastomeric system is hydrophobic.

21. The intravaginal drug delivery device of claim 19, wherein said antimicrobial agent is dispersed homogeneously.

22. The intravaginal drug delivery device of claim 19, wherein said ring has a cross-sectional diameter of about 6–14 mm.

23. The intravaginal drug delivery device of claim 22, wherein said ring has an outer diameter of about 50–60 mm.

24. The intravaginal drug delivery device of claim 19, wherein said Metronidazole, prodrug or salt thereof, is released at a substantially first order rate of about 5 to about 250 mg during said initial 24 hours period of use.

25. The intravaginal drug delivery device of claim 24, wherein said Metronidazole, prodrug or salt thereof is released at a substantially zero order rate of about 3 to about 175 mg per day over a period for at least 3 days, after the initial 24 hour period of use.

26. The intravaginal drug delivery device of claim 19, wherein said Metronidazole, prodrug or salt thereof, is present in an amount in a range of about 0.5 to about 80 weight percent of said device.

27. The intravaginal drug delivery device of claim 20, wherein said hydrophobic elastomeric system is a silicone polymer.

28. The intravaginal drug delivery device of claim 27, wherein said silicone polymer is crosslinked.

29. The intravaginal drug delivery device of claim 19, further comprising a release enhancing excipient.

30. The intravaginal drug delivery device of claim 29, wherein said release enhancing excipient is selected from the group consisting of polyvinylpyrrolidone, modified cellulose ethers, microcrystalline cellulose, polyacrylic acid, carbomer, alginic acid, carrageenan, cyclodextrins, dextrin, guar gum, gelatin, xanthan gum, monosaccharides and disaccharides.

31. The intravaginal drug delivery device of claim 19, wherein a particle size distribution of the Metronidazole, prodrug or salt thereof is 90% particles of less than 200 microns and 50% particles of less than 50 microns.

32. The method of manufacturing an intravaginal antimicrobial drug delivery device comprising the steps:
   (a) mixing a biocompatible elastomer with at least one antimicrobial agent in at least a therapeutically effective amount; and
   (b) curing said mixture in a shape of said intravaginal drug delivery devices,
   wherein said delivery device consists essentially of a ring.

33. The method according to claim 32, wherein the biocompatible elastomer is hydrophobic.

34. The method according to claim 33, wherein said biocompatible hydrophobic elastomer is a silicone polymer.

35. The method according to claim 32, wherein the mixture of biocompatible elastomer and antimicrobial agent includes a crosslinking agent.

36. The method according to claim 32, wherein said antimicrobial agent is selected from the group consisting of Metronidazole, Acyclovir, Clotrimazole, Fluconazole, Terconazole, Azithromycin, Erythromycin, Doxycycline, Tetracycline, Minocycline, Clindamycin, Fanicyclovir, Valacyclovir, Clarithromycin, a prodrug or salt thereof and combinations thereof.

37. The method according to claim 32, wherein said antimicrobial agent is Metronidazole, a produg or salt thereof.

38. The method according to claim 32, wherein the mixture of biocompatible hydrophobic elastomer and antimicrobial agent includes a release enhancing excipient.

39. The method according to claim 38, wherein said release enhancing excipient is selected from the group consisting of polyvinylpyrrolidone, modified cellulose ethers, microcrystalline cellulose, polyacrylic acid, carbomer, alginic acid, carrageenan, cyclodextrins, dextrin, guar gum, gelatin, xanthan gum, monosaccharides and disaccharides.

40. An intravaginal antimicrobial drug delivery device comprising:
   a therapeutically effective amount of at least one antimicrobial agent dispersed throughout a biocompatible elastomeric system that forms said delivery device,
   wherein said antimicrobial agent is released at a substantially first order release rate during an initial twenty four hour period of use.

41. An intravaginal antimicrobial drug delivery device comprising:
   a therapeutically effective amount of at least one antimicrobial agent dispersed throughout a biocompatible elastomeric system that forms said delivery device,
   wherein the solubility in distilled water of said antimicrobial agent is not less than 1 $\mu$g/100 ml at 20° C.

42. An intravaginal antimicrobial drug delivery device comprising:
   a therapeutically effective amount of at least one antimicrobial agent dispersed throughout a biocompatible elastomeric system that forms said delivery device,
   wherein a particle size distribution of the antimicrobial agent is 90% particles of less than 200 microns and 50% particles of less than 50 microns.

* * * * *

UNITED STATES PATENT AND TRADEMARK OFFICE
CERTIFICATE OF CORRECTION

| | | |
|---|---|---|
| PATENT NO. | : 6,951,654 B2 | |
| APPLICATION NO. | : 10/107997 | |
| DATED | : October 4, 2005 | |
| INVENTOR(S) | : Karl Malcolm et al. | |

It is certified that error appears in the above-identified patent and that said Letters Patent is hereby corrected as shown below:

ON THE TITLE PAGE ITEM [75]:

Inventors, "Karl Malcolm, Belfast (IE); David Woolfson, Belfast (IE); Grant Elliott, Islandmagee (IE); Martin Shephard, Belfast (IE)" should read --"Karl Malcolm, Belfast (UK); David Woolfson, Belfast (UK); Grant Elliott, Islandmagee (UK); Martin Shephard, Belfast (UK)"--.

COLUMN 4:

Line 22, "twenty " should read --twenty- --.

COLUMN 6:

Line 58, "and" should be deleted.

COLUMN 9:

Line 5, "dclinically" should read --clinically--.

COLUMN 15:

Line 67, "Am" should read --µm--.

COLUMN 17:

Line 7, "(ug/day)" should read --(µg/day)--.

COLUMN 18:

Line 12, "part" should read --part by--.

UNITED STATES PATENT AND TRADEMARK OFFICE
CERTIFICATE OF CORRECTION

| | |
|---|---|
| PATENT NO. | : 6,951,654 B2 |
| APPLICATION NO. | : 10/107997 |
| DATED | : October 4, 2005 |
| INVENTOR(S) | : Karl Malcolm et al. |

It is certified that error appears in the above-identified patent and that said Letters Patent is hereby corrected as shown below:

<u>COLUMN 21</u>:

Claim 32, Line 15, "steps:" should read --steps of:--.

Signed and Sealed this

Tenth Day of July, 2007

JON W. DUDAS
*Director of the United States Patent and Trademark Office*